(12) United States Patent
Prusiner et al.

(10) Patent No.: US 6,419,916 B1
(45) Date of Patent: *Jul. 16, 2002

(54) ASSAY FOR COMPOUNDS WHICH AFFECT CONFORMATIONALLY ALTERED PROTEINS

(75) Inventors: Stanley B. Prusiner; Surachai Supattapone; Michael R. Scott, all of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/406,972

(22) Filed: Sep. 28, 1999

Related U.S. Application Data

(63) Continuation-in-part of application No. 09/322,903, filed on Jun. 1, 1999, now Pat. No. 6,214,366.

(51) Int. Cl.[7] .............................................. A61K 31/785
(52) U.S. Cl. .................... 424/78.32; 424/78.35; 424/78.36; 424/78.37; 424/78.38; 424/DIG. 16
(58) Field of Search ..................... 424/78.16, 78.32, 424/78.35–78.38; 514/772.3–732.7; 435/238, 339; 523/105, 122

(56) References Cited

U.S. PATENT DOCUMENTS

| | | |
|---|---|---|
| 4,587,329 A | 5/1986 | Tomalia et al. |
| 5,499,979 A | 3/1996 | Wong et al. |
| 5,834,020 A | 11/1998 | Margerum et al. |
| 5,919,442 A | 7/1999 | Yin et al. |

FOREIGN PATENT DOCUMENTS

| | | |
|---|---|---|
| WO | WO 98/15297 | 4/1998 |
| WO | WO 98/32334 | 7/1998 |
| WO | WO 99/42102 | 8/1999 |
| WO | WO 00/65344 | 11/2000 |

OTHER PUBLICATIONS

Basler et al., "Scrapie and Cellular PrP Isoforms Are Encoded by the Same Chromosomal Gene," *Cell*, (Aug. 1, 1989), 46:417–28.

Bruce, et al., "Transmissions to Mice Indicate that 'New Variant' CJD is Caused by the BSE Agent," *Nature*, (1997) 389:498–501.

Combs et al, "Identification of Microglial Signal Transduction Pathways Mediating a Neruotoxic Response to Amyloidogenic Fragments of β–Amyloid and Prion Proteins," *The Journal of Neuroscience*, (Feb. 1, 1999) 19(3):928–939.

Cousens et al., "Predicting the CJD Epidemic in Humans," *Nature*, (1997) 385:197–198.

Gajdusek et al., "Experimental Transmission of a Kuru–like Syndrome to Chimpanzees," *Nature*, (1966) 209:794–796.

Gajdusek "Unconventional Viruses and the Origin and Disappearance of Kuru" *Science* (Sep. 2, 1977), 197(4307):943–960.

(List continued on next page.)

*Primary Examiner*—Neil S. Levy
(74) *Attorney, Agent, or Firm*—Karl Bozicevic; Bozicevic, Field & Francis LLP

(57) ABSTRACT

An assay comprises contacting cells containing a conformationally altered protein with test compound and determining if the altered protein is cleared. The cells may be scrapie-infected neuroblastoma cells. Another assay comprises contacting organ or tissue homogenate (at pH 5.0 or less) with test compound to determine if altered protein in the homogenate is 10 cleared. The homogenate may be brain homogenate from a transgenic mouse infected with human prions. Compounds which are found to clear the altered protein are useful in preventing, arresting and/or reversing (i.e. treating) a disease associated with the conformationally altered protein.

8 Claims, 1 Drawing Sheet

OTHER PUBLICATIONS

Gibbs et al., "Creutzfeldt–Jakob Disease (Spongiform Encephalopathy): Transmission to the Chimpanzes," *Science*, (1968) 161:388–389.

Glenner et al., "Amyloidosis of the nervous system" *J. Neurol. Sci.* (1989) 94:1–28.

Goldfarb et al., "Fatal Familial Insomnia and Familial Creutzfeldt–Jakob Disease: Disease Phenotype Determined by a DNA Polymorphism," *Science*, (1992) 258:806–808.

Haan et al. "Amyloid in Central Nervous System Disease," *Clin. Neurol Neurosurg.* (1990) 92(4):305–310.

Hardy, "Amyloid, the Presenilins and Alzheimer's Disease," *Trends Neurosci.* (1997) 20(4):154–159.

Hill, et al., "The Same Prion Strain Causes vCJD and BSE," *Nature*, (1997) 389:448–450.

Ingrosso, et al., "Congo red Prolongs the Incubation Period in Scrapie–Infected Hamsters," *J. Virol.*, (1995) 69:506–508.

Kalaria et al., Differential Degeneration of the Cerebral Microvasculature in Alzheimer's Disease *NeuroReport* (1995) 6:477–480.

Kawai et al. "Degeneration of Vascular Muscle Cells in Cerebral Amyloid Angiopathy of Alzheimer's Disease." *Brain Res*, 623:142–146.

Kelly, "Alternative Conformations of Amyloidogenic Proteins Govern Their Behavior," *Current Opinions in Structural Biology*, (1996) *Strut Biol* 6(1):11–17.

Ladogana, et al., "Sulphate Polyanions Prolong the Incubation Period of Scrapie–Infected Hamsters," *J. Gen. Virol.*, (1992) 73:661–665.

Lai, et al., "The Acid–Mediated Denaturation Pathway of Transthyretin Yields a Conformational Intermediate Than Can Self–Assemble into any Amyloid," *Biochemistry*, (1996), 35(20):6470–6482.

Lasmézas, et al., "BSE Transmission to Macaques," *Nature*, (1996) 381:743–744.

Lendon et al., "Exploring the Etiology of Alzheimer Disease Using Molecular Genetics," *J. Am. Med. Assoc.*, (1997), 277(10):825–831.

Mandybur, "Cerebral Anyloid Angiopathy and Astroc Glisos in Alzheimer's Disease," *Acta Neuropath.*, (1989) 78:329–331.

Martin et al., "Synaptic Pathology and Glial Responses to Neuronal Injury Precede the Formation of Senile Plaques and Amyloid Deposits in the Aging Cerebral Cortex," *Amer. Journal of Pathology*, (1994) 145(6):1358–1381.

Masliah et al., "Comparison of Neurodegenerative Pathology in Transgenic Mice Overexpressing V717F β–Amyloid Precursor Protein and Alzheimer's Disease," *Journal of Neuroscience*, (Sep. 1996) 16(18):5795–5811.

Masullo, et al., "Failure to Ameliorate Creutzfeldt–Jakob Disease with Amphotericin B Therapy," *J. Infec. Dis.*, (1992) 165:784–785.

McCutchen, et al., "Transthyretin Mutation Leu–55–Pro Significantly Alters Tetramer Stability and Increases Amyloidogenicity," *Biochemistry*, (1993) 32(45):12119–12127.

McCutchen, et al., "Intermolecular Disulfide Linkages Are Not Required for Transthyretin Amyloid Fibril Formation in Vitro," *Biochem., Biophys. Res. Commun*, (1993) 197(2) 415–21.

Medori et al., Fatal Familial Insomnia, A Prion Disease With a Mutation at Codon 178 of The Prion Protein Gene, *New. England Journal of Medicine*, (Feb. 13, 1992), 326(7):444–449.

Medori, et al., "Fatal Familial Insomnia: A Second Kindred with Mutation of Prion Protein Gene of codon 178," *Neurology*, (1992) 42:669–670.

Miroy, "Inhibiting Transthyretin Amyloid Fibril Formation via Protein Stabilization," *Proc. Natl. Acad. Sci. USA*, (Dec. 1996), 93(26):15051–15056.

Pan, et al., "Conversion of α–Helices into β–Sheets Features in the Formation of the Scrapie Prion Proteins," *Proc. Natl. Acad. Sci. USA*, (1993), 90:10962–10966.

Prusiner, et al., "Prions," *Proc. Natl. Acad. Sci. USA*, (1998), 95:13363–13383.

Prusiner, "Biology of Prions," *The Molecular and Genetic Basis of Neurological Disease*, 2nd Edition, Ch. 7., (1997), pp. 103–143.

Prusiner, "Scrapie Prions," *Annu. Rev. Microbiol*, (1989) 43:345–374.

Safar, et al., "Conformational Transitions, Dissociation, and Unfolding of Scrapie Amyloid (Prion) Protein," *Journal of Biol. Chem.*, (1993) 268(27):20276–20284.

Selkoe et al., "β–Amyloid Precursor Protein of Alzheimer Disease Occurs as 110– to 135–Kilodalton Membranes–Associated Proteins in Neural and Nonneural Tissues," *Proc. Natl. Acad. Sci. USA*, (1988) 85:7341–7345.

Selkoe, "Physiological Production of the β–Amyloid Protein and the Mechanism of Alzheimer's Disease," *Trends in Neurosciences*, (1993) 16(10):403–409.

Selkoe, "Amyloid β–Protein and the Genetics of Alzheimer's Disease," *Journ. of Biol. Chem.*, (1996), 271(31):18295–8.

Tagliavini, et al., "Effectiveness of Anthracycline Against Experimental Prion Disease in Syrian hamsters," *Science*, (1997) 276:1119–1122.

Wilesmith, et al., "Bovine Spongiform Encephalopathy," *Current Topics in Microbiology and Immunology*, (1991) 172:21–38.

Will, et al., "A New Variant of Creutfeldt–Jakob Disease in the K," *Lancet*, (1996) 347:921–925.

Will, et al., "Deaths from Variant Creutzfeldt–Jakob Disease," *Lancet*, (1999) 353:979.

Yankner, "New Clues to Alzheimer's Disease: Unraveling the Roles of Amyloid and Tau," *Nature Medicine*, (1996) 2(8):850–852.

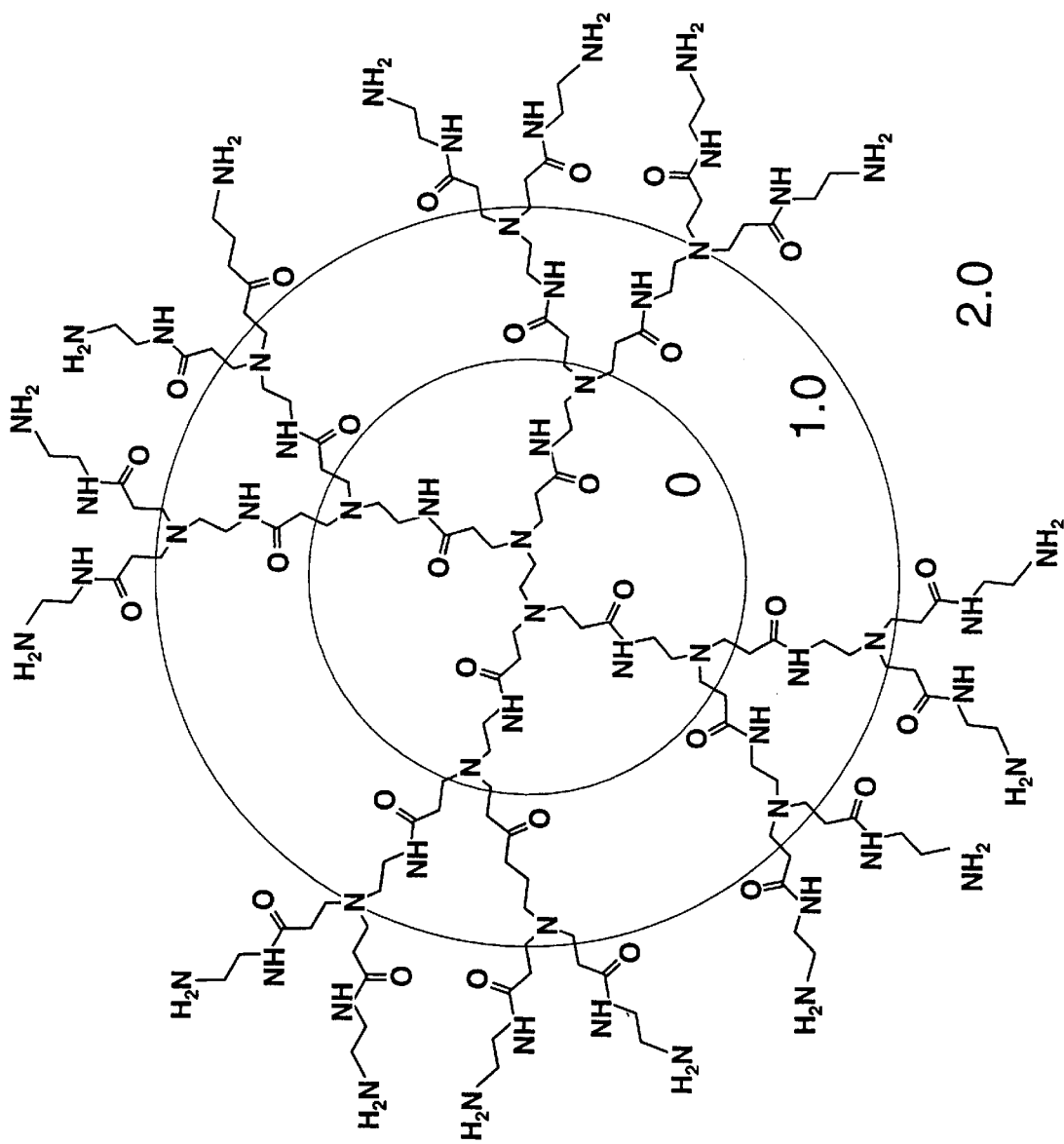

ASSAY FOR COMPOUNDS WHICH AFFECT CONFORMATIONALLY ALTERED PROTEINS

CROSS-REFERENCE

This application is a continuation-in-part of earlier filed application Ser. No. 09/322,903 filed Jun. 1, 1999 U.S. Pat. No. 6,214,366 which application is incorporated herein in its entirety and to which application is claimed priority under 35 U.S.C. §120.

GOVERNMENT SUPPORT

This work was supported, in part, by grants from the National Institutes of Health NS14069, AG08967, AG02132, AG10770 and K08 NS02048-02. The government may have certain rights in this work.

FIELD OF THE INVENTION

The present invention is related generally to assays and more specifically to assays which determine compounds which might provide a therapeutic effect of a disease associated with a conformationally altered protein.

BACKGROUND OF THE INVENTION

There are a considerable number of diseases associated with a conformationally altered protein. For example, Alzheimer's disease is associated with APP, A$\beta$ peptide, $\alpha$1-antichymotrypin, tau and non-A$\beta$ component. Many of these diseases are neurological diseases. However, type II Diabetes is associated with Amylin and Multiple myeloma-plasma cell dyscrasias is associated with IgGL-chain. The relationship between the disease onset and the transition from the normal protein to the conformationally altered protein has been examined very closely in some instances such as with the association between prion diseases and $PrP^{Sc}$.

Prion diseases are a group of fatal neurodegenerative disorders that can occur in hereditary, sporadic, and infectious forms (Prusiner, S. B. Scrapie prions. *Annu. Rev. Microbiol.* 43, 345–374 (1989)). These illnesses occur in humans and a variety of other animals (Prusiner, S. B. Prions. *Proc. Natl. Acad. Sci.* USA 95, 13363–13383 (1998)). Prions are infectious proteins. The normal, cellular form of the prion protein (PrP) designated $PrP^C$ contains three $\alpha$- helices and has little $\beta$- sheet; in contrast, the protein of the prions denoted $PrP^{Sc}$ is rich in $\beta$-sheet structure. The accumulation of $PrP^{Sc}$ in the central nervous system (CNS) precedes neurologic dysfunction accompanied by neuronal vacuolation and astrocytic gliosis.

The spectrum of human prion diseases includes kuru (Gajdusek, D. C., Gibbs, C. J., Jr. & Alpers, M. Experimental transmission of a kuru-like syndrome to chimpanzees. *Nature* 209, 794–796 (1966)), Creutzfeldt-Jakob disease (CJD) (Gibbs, C. J., Jr., et al. Creutzfeldt-Jakob disease (spongiform encephalopathy): transmission to the chimpanzee. *Science* 161, 388–389 (1968)), Gerstmann-Stra̋ussler-Scheinker disease (GSS) and fatal familial insomnia (FFI) (Goldfarb, L. G., et al. Fatal familial insomnia and familial Creutzfeldt-Jakob disease: disease phenotype determined by a DNA polymorphism. *Science* 258, 806–808 (1992); Medori, R., et al. Fatal familial insomnia: a second kindred with mutation of prion protein gene at codon 178. *Neurology* 42, 669–670 (1992)), and a new form of human prion disease, new variant CJD (nvCJD), which has emerged in Great Britain and France (Will, R. G., et al. A new variant of Creutzfeldt-Jakob disease in the UK. *Lancet* 347, 921–925 (1996); Cousens, S. N., Vynnycky, E., Zeidler, M., Will, R. G. & Smith, P. G. Predicting the CJD epidemic in humans. *Nature* 385, 197–198 (1997); Will, R. G., et al. Deaths from variant Creutzfeldt-Jakob disease. *Lancet* 353, 979 (1999)). Several lines of evidence have suggested a link between the nvCJD outbreak and a preceding epidemic of bovine spongiform encephalopathy (BSE) (Will, R. G., et al. A new variant of Creutzfeldt-Jakob disease in the UK. *Lancet* 347, 921–925 (1996); Bruce, M. E., et al. Transmissions to mice indicate that 'new variant' CJD is caused by the BSE agent. *Nature* 389, 498–501 (1997); Hill, A. F., et al. The same prion strain causes vCJD and BSE. *Nature* 389, 448–450 (1997); Lasmézas, C. I., et al. BSE transmission to macaques. *Nature* 381, 743–744 (1996)). Although it is too early to predict the number of nvCJD cases that might eventually arise in Great Britain and elsewhere (Cousens, S. N., Vynnycky, E., Zeidler, M., Will, R. G. & Smith, P. G. Predicting the CJD epidemic in humans. *Nature* 385, 197–198 (1997)), it is clear that effective therapeutics for prion diseases are urgently needed. Unfortunately, although a number of compounds including amphotericins, sulfated polyanions, Congo red dye, and anthracycline antibiotics have been reported as prospective therapeutic agents (Ingrosso, L., Ladogana, A. & Pocchiari, M. Congo red prolongs the incubation period in scrapie-infected hamsters. *J. Virol.* 69, 506–508 (1995); Tagliavini, F., et al. Effectiveness of anthracycline against experimental prion disease in Syrian hamsters. *Science* 276, 1119–1122 (1997); Masullo, C., Macchi, G., Xi, Y. G. & Pocchiari, M. Failure to ameliorate Creutzfeldt-Jakob disease with amphotericin B therapy. *J. Infect. Dis.* 165, 784–785 (1992); Ladogana, A., et al. Sulphate polyanions prolong the incubation period of scrapie-infected hamsters. *J. Gen. Virol.* 73, 661–665 (1992)), all have demonstrated only modest potential to impede prion propagation, and none have been shown to effect the removal of pre-existing prions from an infected host.

The PrP gene of mammals expresses a protein which can be the soluble, non-disease form $PrP^C$ or be converted to the insoluble, disease form $PrP^{Sc}$. $PrP^C$ is encoded by a single-copy host gene [Basler, Oesch et al. (1986) *Cell* 46:417–428] and when $PrP^C$ is expressed it is generally found on the outer surface of neurons. Many lines of evidence indicate that prion diseases result from the transformation of the normal form of prion protein ($PrP^C$) into the abnormal form ($PrP^{Sc}$). There is no detectable difference in the amino acid sequence of the two forms. However, $PrP^{Sc}$ when compared with $PrP^C$ has a conformation with higher $\beta$-sheet and lower $\alpha$-helix content (Pan, Baldwin et al. (1993) *Proc Natl Acad Sci* USA 90:10962–10966; Safar, Roller et al. (1993) *J Biol Chem* 268:20276–20284). The presence of the abnormal $PrP^{Sc}$ form in the brains of infected humans or animals is the only disease-specific diagnostic marker of prion diseases.

$PrP^{Sc}$ plays a key role in both transmission and pathogenesis of prion diseases (spongiform encephalopathies) and it is a critical factor in neuronal degeneration (Prusiner (1997) The Molecular and Genetic Basis of Neurological Disease, 2nd Edition: 103–143). The most common prion diseases in animals are scrapie of sheep and goats and bovine spongiform encephalopathy (BSE) of cattle (Wilesmith and Wells (1991) *Curr Top Microbiol Immunol* 172:21–38). Four prion diseases of humans have been identified: (1) kuru, (2) Creutzfeldt-Jakob Disease (CJD), (3) Gerstmann-Sträussler-Sheinker Disease (GSS), and (4) fatal familial insomnia (FFI) [Gajdusek (1977) *Science*

197:943–960; Medori, Tritschler et al. (1992) *N Engl J Med* 326:444–449]. Initially, the presentation of the inherited human prion diseases posed a conundrum which has since been explained by the cellular genetic origin of PrP.

The assembly and misassembly of normally soluble proteins into conformationally altered proteins is thought to be a causative process in a variety of other diseases. Structural conformational changes are required for the conversion of a normally soluble and functional protein into a defined, insoluble state. Examples of such insoluble protein include: Aβ peptide in amyloid plaques of Alzheimer's disease and cerebral amyloid angiopathy (CAA); α-synuclein deposits in Lewy bodies of Parkinson's disease, tau in neurofibrillary tangles in frontal temporal dementia and Pick's disease; superoxide dismutase in amyotrophic lateral sclerosis; huntingtin in Huntington's disease; and prions in Creutzfeldt-Jakob disease (CJD): (for reviews, see Glenner et al. (1989) *J. Neurol. Sci.* 94:1–28; Haan et al. (1990) *Clin. Neurol. Neurosurg.* 92(4):305–310).

Often these highly insoluble proteins form aggregates composed of nonbranching fibrils with the common characteristic of a β-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions (Mandybur (1989) *Acta Neuropathol.* 78:329–331; Kawai et al. (1993) *Brain Res.* 623:142–6; Martin et al. (1994) *Am. J. Pathol.* 145:1348–1381; Kalaria et al. (1995) *Neuroreport* 6:477–80; Masliah et al. (1996) *J. Neurosci.* 16:5795–5811). Other studies additionally indicate that amyloid fibrils may actually initiate neurodegeneration (Lendon et al. (1997) *J. Am. Med. Assoc.* 277:825–31; Yankner (1996) *Nat. Med.* 2:850–2; Selkoe (1996) *J. Biol. Chem.* 271:18295–8; Hardy (1997) *Trends Neurosci.* 20:154–9).

In both AD and CAA, the main amyloid component is the amyloid β protein (Aβ). The Aβ peptide, which is generated from the amyloid β precursor protein (APP) by two putative secretases, is present at low levels in the normal CNS and blood. Two major variants, $A\beta_{1-40}$ and $A\beta_{1-42}$, are produced by alternative carboxy-terminal truncation of APP (Selkoe et al.(1988) *Proc. Natl. Acad. Sci. USA* 85:7341–7345; Selkoe, (1993) *Trends Neurosci* 16:403–409). $A\beta_{1-42}$ is the more fibrillogenic and more abundant of the two peptides in amyloid deposits of both AD and CAA. In addition to the amyloid deposits in AD cases described above, most AD cases are also associated with amyloid deposition in the vascular walls (Hardy (1997), supra; Haan et al. (1990), supra; Terry et al., supra; Vinters (1987), supra; Itoh et al. (1993), supra; Yamada et al. (1993), supra; Greenberg et al. (1993), supra; Levy et al. (1990), supra). These vascular lesions are the hallmark of CAA, which can exist in the absence of AD.

Human transthyretin (TTR) is a normal plasma protein composed of four identical, predominantly β-sheet structured units, and serves as a transporter of hormone thyroxin. Abnormal self assembly of TTR into amyloid fibrils causes two forms of human diseases, namely senile systemic amyloidosis (SSA) and familial amyloid polyneuropathy (FAP) (Kelly (1996) *Curr Opin Strut Biol* 6(1):11–7). The cause of amyloid formation in FAP are point mutations in the TTR gene; the cause of SSA is unknown. The clinical diagnosis is established histologically by detecting deposits of amyloid in situ in bioptic material.

To date, little is known about the mechanism of TTR conversion into amyloid in vivo. However, several laboratories have demonstrated that amyloid conversion may be simulated in vitro by partial denaturation of normal human TTR [McCutchen, Colon et al. (1993) *Biochemistry* 32(45) :12119–27; McCutchen and Kelly (1993) *Biochem Biophys Res Commun* 197(2) 415–21]. The mechanism of conformational transition involves monomeric conformational intermediate which polymerizes into linear β-sheet structured amyloid fibrils [Lai, Colon et al. (1996) *Biochemistry* 35(20):6470–82]. The process can be mitigated by binding with stabilizing molecules such as thyroxin or triiodophenol (Miroy, Lai et al. (1996) *Proc Natl Acad Sci USA* 93(26) :15051–6).

The precise mechanisms by which neuritic plaques are formed and the relationship of plaque formation to the disease-associated neurodegenerative processes are not well-defined. The amyloid fibrils in the brains of Alzheimer's and prion disease patients are known to result in the inflammatory activation of certain cells. For example, primary microglial cultures and the THP-1 monocytic cell line are stimulated by fibrillar β-amyloid and prion peptides to activate identical tyrosine kinase-dependent inflammatory signal transduction cascades. The signaling response elicited by β-amyloid and prion fibrils leads to the production of neurotoxic products, which are in part responsible for the neurodegenerative. C. K. Combs et al, *J Neurosci* 19:928–39 (1999).

Despite considerable efforts effective therapeutic compounds for the treatment of diseases associated with conformationally altered protein have not been discovered. The present invention offers an assay for identifying therapeutic compounds and further disclose a class of compounds which have been shown to be effective in clearing deposits of conformationally altered proteins associated with disease.

BRIEF DESCRIPTION OF THE DRAWING

FIG. 1 is a schematic drawing of a dendrimer molecule showing the defined "generations" of homodisperse structure created using a repetitive divergent growth technique. The specific diagram is of PAMAM, generation 2.0 (ethylene diamine core).

SUMMARY OF THE INVENTION

An assay is provided whereby compounds are tested to determine their potential efficacy as therapeutics for the treatment of disorders associated with conformationally altered protein, e.g. prion diseases associated with the $PrP^{Sc}$ conformation of a PrP protein. The assay comprises contacting scrapie-infected neuroblastoma (ScN2a) cells in culture with a test compound to determine if the test compound reduces levels of $PrP^{Sc}$. Preferably the assay includes a plurality of tests wherein different concentrations of the test compounds are separately contacted with different portions of the same cell culture and further wherein different cell cultures are contacted with the test compound for a plurality of different exposure times prior to testing for $PrP^{Sc}$ levels.

In another embodiment of the assay of the invention an organ homogenate (e.g. a brain homogenate) is provided which homogenate comprises conformationally altered proteins, i.e. comprises $PrP^{Sc}$ particles. The pH of the homogenate is then reduced to a pH of about 4.0±1.0 and a test compound is added to determine if the test compound reduces levels of the conformationally altered protein (e.g., $PrP^{Sc}$) in the homogenate. The assay preferably comprises a plurality of tests wherein different concentrations of the test compound are separately contacted with different portions of the same homogenate and farther wherein the test compound is brought into contact with the different portions of a homogenate for different exposure times prior to testing for conformationally altered protein levels.

In any assay of the invention the results obtained in terms of reduced levels of conformationally altered protein (e.g., $PrP^{Sc}$) obtained using a test compound can be compared to negative and positive controls with the positive control being a highly-branched polycation.

In addition to assays the present invention provides methods of arresting, preventing and/or reversing the impairment of physiologic systems, the methods comprising reducing the burden of insoluble protein deposits by the administration of branched polycationic agents or pharmaceutical compositions containing such branched polycationic agents. The agents used in the preferred method of the invention are highly-branched polycations, e.g. dendritic polycations.

In one embodiment, the invention provides pharmaceutical compositions for the treatment of protein deposit formation in an animal which compositions contain branched polycations agents, preferably highly-branched polycations. Branched polycations for use in the invention include, but are not limited to, polypropylene imine, polyethyleneimine (PEI) poly(4'-aza-4'-methylheptamethylene D-glucaramide), polyamidoamines and suitable fragments and/or variants of these compounds. The pharmaceutical compositions can also contain other active ingredients, either separate or complexed to the branched polycations.

The invention also provides methods for reducing the burden of insoluble protein deposits in various host tissues by administering a highly-branched polycationic agent to the host. Preferably the highly-branched polycation is administered over a period of time, either continuously or in multiple dosage units. The animal treated may be suffering from any degenerative disorder associated with insoluble protein deposits. For example, the animal may be a human suffering from Alzheimer's Disease or a cow suffering from BSE.

The invention also features a method for reversing protein deposits in degenerative diseases of a subject by administration of a polycationic compound. The compound is preferably a highly-branched polycation, and the subject may be suffering from degenerative disorder.

The invention also features a method for preventing the formation of protein deposits in animals or humans at risk for a degenerative disease by administration of a highly-branched polycationic compound in an amount sufficient to suppress formation of the protein deposits. The compound used in this method is preferably a highly-branched polycation. Subjects for treatment with this method may be genetically predisposed to developing degenerative disease, such as humans genetically at risk for AD, Parkinson's disease, ALS, FTD, Pick's disease, Huntington's disease or CJD. Subjects may also be determined to be at risk due to exposure to infectious agents causing amyloid-associated disorders, e.g. cattle exposed to bovine prions from a BSE contaminated source.

An object of the invention is to provide an assay for identifying compounds which affect conformationally altered proteins and particularly which aid in reducing levels of such proteins in a low pH environment.

An aspect of the invention is an assay whereby a scrapie-infected neuroblastoma (ScN2a) cell culture is contacted with a test compound to determine if the test compound can reduce the $PrP^{Sc}$ level in the cell culture.

Another aspect of the invention is an assay whereby organ (e.g. brain) homogenate is reduced to a pH of less than 5 and contacted with a test compound to determine if the test compound can reduce the level of conformationally altered protein (e.g. $PrP^{Sc}$) in the homogenate.

An advantage of the invention is that the basic methodology is applicable to assaying for compounds with potential therapeutic utility for a wide range of diseases associated with conformationally altered proteins.

A feature of the compounds of the present invention is their ability to mediate the clearance of $PrP^{Sc}$ from cultured cells under non-cytotoxic conditions.

An advantage of the pharmaceutical compositions of the invention is that the highly-branched polycation administered is non-toxic to the mammalian host at a dosage of 0.001 mg to 1 mg/kg body weight per day.

Another advantage is that subjects treated with the methods of invention remain free of insoluble protein deposits after clearance.

These and other objects, advantages, and features of the invention will become apparent to those persons skilled in the art upon reading the details of the compounds, and assay method more fully described below.

DETAILED DESCRIPTION OF PREFERRED EMBODIMENTS

Before the present assays, compounds and methods of use are described, it is to be understood that this invention is not limited to particular assay steps, compounds, modes of administration and the like described and, as such, may of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "conformationally altered protein" is used here to describe any protein which has a three dimensional conformation associated with a disease. The conformationally altered protein may cause the disease, be a factor in a symptom of the disease or appear as a result of other factors. The conformationally altered protein appears in another conformation which has the same amino acid sequence. In general, the conformationally altered protein formed is "constricted" in conformation as compared to the other "relaxed" conformation which is not associated with disease. The following is a non-limiting list of diseases with associated proteins which assemble two or more different conformations wherein at least one conformation is an example of a conformationally altered protein.

| Disease | Insoluble Proteins |
| --- | --- |
| Alzheimer's Disease | APP, Aβ peptide, α1-ntichymotrypsin, tau, non-Aβ component, presenilin 1, presenilin 2 apoE |
| Prion diseases, Creutzfeld Jakob disease, scrapie and bovine spongiform encephalopathy | PrP$^{Sc}$ |
| ALS | SOD and neurofilament |
| Pick's disease | Pick body |
| Parkinson's disease | α-synuclein in Lewy bodies |
| Frontotemporal dementia | tau in fibrils |
| Diabetes Type II | Amylin |
| Multiple myeloma--plasma cell dyscrasias | IgGL-chain |
| Familial amyloidotic polyneuropathy | Transthyretin |
| Medullary carcinoma of thyroid | Procalcitonin |
| Chronic renal failure | $\beta_2$--microglobulin |
| Congestive heart failure | Atrial natriuretic factor |
| Senile cardiac and systemic amyloidosis | Transthyretin |
| Chronic inflammation | Serum amyloid A |
| Atherosclerosis | ApoA1 |
| Familial amyloidosis | Gelsolin |
| Huntington's disease | Huntingtin |

The terms "treatment", "treating", "treat" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in an animal, particularly a human, and includes:

(a) preventing the disease or symptom from occurring in a subject which may be predisposed to the disease or symptom but has not yet been diagnosed as having it;

(b) inhibiting the disease of its symptom, i.e., arresting development of the disease or its symptoms; or (c) relieving the disease symptom, i.e., causing regression of the disease or symptom.

By "effective dose" or "amount effective" is meant an administration of a compound sufficient to provide the desired physiological and/or psychological change. This will vary depending on the patient, the disease and the treatment. The dose may either be a therapeutic dose, in which case it should sufficiently alter levels of insoluble protein deposits in the subject to alleviate or ameliorate the symptoms of the disorder or condition, or a prophylactic dose, which should be sufficient to prevent accumulation of insoluble protein deposits to an undesirable level.

The terms "compound," "test compound" and the like are used here to describe any molecule. Examples of such molecules include any protein or small molecule pharmaceutical, polymer, salt or the like. Preferred compounds have the capability of affecting molecular and clinical phenomena which is preferably associated with a disease, e.g. associated with amyloid-associated disorders, and particularly AD, CAA, and prion-mediated disorders.

The term "diagnosis" is used herein to cover any type of analysis used to determine or project a status which includes identification of a disease from its symptoms and determining the presence of molecules associated with a disorder (e.g., PrP$^{Sc}$ for CJD, increased apoE levels for AD) in an area (e.g., brain tissue) which suggest a disease status.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "LD$_{50}$" as used herein is the dose of an active substance that will result in 50 percent lethality in all treated experimental animals. Although this usually refers to invasive administration, such as oral, parenteral, and the like, it may also apply to toxicity using less invasive methods of administration, such as topical applications of the active substance.

The term "amine-terminated" includes primary, secondary and tertiary amines.

The terms "PrP protein", "PrP" and like are used interchangeably herein and shall mean both the infectious particle form PrP$^{Sc}$ known to cause diseases (spongiform encephalopathies) in humans and animals and the noninfectious form PrP$^{C}$ which, under appropriate conditions is converted to the infectious PrP$^{Sc}$ form.

The terms "prion", "prion protein", "PrP$^{Sc}$ protein" and the like are used interchangeably herein to refer to the infectious PrP$^{Sc}$ form of a PrP protein, and is a contraction of the words "protein" and "infection." Particles are comprised largely, if not exclusively, of PrP$^{Sc}$ molecules encoded by a PrP gene. Prions are distinct from bacteria, viruses and viroids. Known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI). As used herein "prion" includes all forms of prions causing all or any of these diseases or others in any animals used—and in particular in humans and domesticated farm animals.

The term "PrP gene" is used herein to describe genetic material which expresses proteins including known polymorphisms and pathogenic mutations. The term "PrP gene" refers generally to any gene of any species which encodes any form of a prion protein. Some commonly known PrP sequences are described in Gabriel et al., *Proc. Natl. Acad. Sci. USA* 89:9097–9101 (1992) and U.S. Pat. No. 5,565,186, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a PrP$^{C}$ (non-disease) or PrP$^{Sc}$ (disease) form.

The terms "standardized prion preparation", "prion preparation", "preparation" and the like are used interchangeably herein to describe a composition (e.g., brain homogenate) obtained from the brain tissue of mammals which exhibits signs of prion disease: the mammal may (1)

include a transgene as described herein; (2) have and ablated endogenous prion protein gene; (3) have a high number of prion protein gene from a genetically diverse species; and/or (4) be a hybrid with an ablated endogenous prion protein gene and a prion protein gene from a genetically diverse species. Different combinations of 1–4 are possible, e.g., 1 and 2. The mammals from which standardized prion preparations are obtained exhibit clinical signs of CNS dysfunction as a result of inoculation with prions and/or due to developing the disease of their genetically modified make up, e.g., high copy number of prion protein genes. Standardized prion preparations and methods of making such are described and disclosed in U.S. Pat. No. 5,908,969 issued Jun. 1, 1999 and application Ser. No. 09/199,523 filed Nov. 25, 1998 both of which are incorporated herein by reference in their entirety to disclose and describe standardized prion preparations.

The term "Alzheimer's disease" (abbreviated herein as "AD") as used herein refers to a condition associated with formation of neuritic plaques comprising amyloid β protein, primarily in the hippocampus and cerebral cortex, as well as impairment in both learning and memory. "AD" as used herein is meant to encompass both AD as well as AD-type pathologies.

The term "AD-type pathology" as used herein refers to a combination of CNS alterations including, but not limited to, formation of neuritic plaques containing amyloid β protein in the hippocampus and cerebral cortex. Such AD-type pathologies can include, but are not necessarily limited to, disorders associated with aberrant expression and/or deposition of APP, overexpression of APP, expression of aberrant APP gene products, and other phenomena associated with AD. Exemplary AD-type pathologies include, but are not necessarily limited to, AD-type pathologies associated with Down's syndrome that is associated with overexpression of APP.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics.

The term "cerebral amyloid angiopathy" (abbreviated herein as CAA) as used herein refers to a condition associated with formation of amyloid deposition within cerebral vessels which can be complicated by cerebral parenchymal hemorrhage. CAA is also associated with increased risk of stroke as well as development of cerebellar and subarachnoid hemorrhages (Vinters (1987) *Stroke* 18:311–324; Haan et al. (1994) *Dementia* 5:210–213; Itoh et al. (1993) *J. Neurol. Sci.* 116:135–414). CAA can also be associated with dementia prior to onset of hemorrhages. The vascular amyloid deposits associated with CAA can exist in the absence of AD, but are more frequently associated with AD.

The term "phenomenon associated with cerebral amyloid angiopathy" as used herein refers to a molecular, structural, or functional event associated with CAA, particularly such an event that is readily assessable in an animal model. Such events include, but are not limited to, amyloid deposition, cerebral parenchymal hemorrhage, and other CAA-associated characteristics.

The term "β-amyloid deposit" as used herein refers to a deposit in the brain composed of Aβ as well as other substances. Abbreviations used herein include:

CNS for central nervous system;
BSE for bovine spongiform encephalopathy;
CJD for Creutzfeldt-Jacob Disease;
FFI for fatal familial insomnia;
GSS for Gerstmann-Sträussler-Scheinker Disease;
AD for Alzheimer's disease;
CAA for cerebral amyloid angiopathy;
Hu for human;
HuPrP for human prion protein;
Mo for mouse;
MoPrP for mouse prion protein;
SHa for a Syrian hamster;
SHaPrP for a Syrian hamster prion protein;
PAMAM for polyamidoamide dendrimers
PEI for polyethyleneimine
PPI for polypropyleneimine
$PrP^{SC}$ for the scrapie isoform of the prion protein;
$PrP^{C}$ for the cellular contained common, normal isoform of the prion protein;
PrP 27–30 or $PrP^{Sc}$ 27–30 for the treatment or protease resistant form of $PrP^{Sc}$;
$MoPrP^{Sc}$ for the scrapie isoform of the mouse prion protein;
N2a for an established neuroblastoma cell line used in the present studies;
ScN2a for a chronically scrapie-infected neuroblastoma cell line;
ALS for amyotrophic lateral sclerosis;
HD for Huntington's disease;
FTD for frontotemporal dementia;
SOD for superoxide dismutase

GENERAL ASPECTS OF THE INVENTION

The invention includes assays for finding compounds, the compounds themselves and formulations containing the compounds and methods of treatment carried out using the compounds and formulations. The assay method includes a method based on the use of an organ (e.g. brain) homogenate and a cell culture. In that the mechanism on which the homogenate based assay is founded was discovered by understanding the cell culture assay, the specifics of the cell culture system is described below first.

The assay could be carried out on the tissue or organ (e.g. brain) homogenate of any animal—preferably a human that died of the disease of interest. More preferably, the homogenate is a standardized homogenate which could be obtained from a transgenic animal (e.g. mouse) engineered to produce the conformationally altered protein of interest. Such transgenic mice are taught in U.S. Pat. Nos. 5,565,186; 5,763,740; and 5,792,901. The standardized homogenate made from such mice are taught in U.S. Pat. No. 5,908,969. The presence of the conformationally altered protein in the homogenate before and after exposure to the test compound could be made by any known method, e.g. using labeled antibodies—see U.S. Pat. No. 5,846,533. A preferred method is taught in U.S. Pat. No. 5,891,641. Each of the above cited patents is incorporated herein in its entirety to disclose and describe the subject matter it is cited in connection with.

ScN2a CELL BASED ASSAY

Efforts were made to optimize the transfection of ScN2a cells with pSPOX expression plasmids (Scott, M. R., Kohler, R., Foster, D. & Prusiner, S. B. Chimeric prion protein expression in cultured cells and transgenic mice. *Protein Sci.* 1, 986–997 (1992)). In connection with those effects an evaluation was made of a transfection protocol that used SuperFect reagent (QIAGEN®). It was found that epitope-tagged (MHM2) PrP$^{Sc}$ (Scott, M. R., Köhler, R., Foster, D. & Prusiner, S. B. Chimeric prion protein expression in cultured cells and transgenic mice. *Protein Sci.* 1, 986–997 (1992)) could not be detected in ScN2a cells following SuperFect-mediated transfection, whereas MHM2 PrP$^{Sc}$ was efficiently formed when a cationic liposome method for DNA delivery was used. Close scrutiny revealed that, prior to protease digestion, SuperFect-transfected samples expressed MHM2 bands, which are not seen in the background pattern of an untransfected sample. The 3F4 monoclonal antibody does not react with MoPrP but does exhibit high background staining on Western blots of mouse ScN2a cells. Inicreased immuno staining in the 20–30 kDa region was observed compared to the non-transfected sample. These observations led us to conclude that MHM2 PrP was successfully expressed using SuperFect transfection reagent, but that conversion of MH2 PrP$^C$ to protease-resistant MHM2 PrP$^{Sc}$ was inhibited by SuperFect.

To investigate this apparent inhibition, a Western blot was reprobed with RO73 polyclonal antiserum to detect endogenous MoPrP$^{Sc}$, the presence of which is diagnostic for prion infection in ScN2a cells (Butler, D. A., et al. Scrapie-infected murine neuroblastoma cells produce protease-resistant prion proteins. *J. Virol.* 62, 1558–1564 (1988)). Surprisingly, it was found that the SuperFect-treated ScN2a cells no longer contained detectable quantities of MoPrP$^{Sc}$—also confirmed in Western blots. To investigate the mechanism by which SuperFect reduced the level of pre-existing PrP$^{Sc}$ in chronically infected ScN2a cells, measurements were made of endogenous PrP$^{Sc}$ in ScN2a cells exposed to various concentrations of SuperFect in the absence of plasmid DNA. The results showed that treatment with SuperFect caused the disappearance of PrP$^{Sc}$ from ScN2a cells in a dose-dependent manner. The concentration of SuperFect required to eliminate >95 % of pre-existing PrP$^{Sc}$ with a three hour exposure was found to be about 150 μg/ml. Duration of treatment also influenced the ability of SuperFect to remove PrP$^{Sc}$ from ScN2a cells: exposure to 150 μg/ml SuperFect for 10 min did not affect PrP$^{Sc}$ levels, whereas 7.5 μg/ml SuperFect eliminated all detectable PrP$^{Sc}$ with a t½=8 h.

SuperFect is a mixture of branched polyamines derived from heat-induced degradation of a PAMAM dendrimer (Tang, M. X., Redemann, C. T. & Szoka, F. C. J. In vitro gene delivery by degraded polyamidoamine dendrimers. *Bioconjug. Chem.* 7, 703–714 (1996)). Knowing this structure the ability of several other branched and unbranched polymers to eliminate PrP$^{Sc}$ from ScN2a cells (Table 1). The branched polymers investigated include various preparations of PEI, as well as intact PAMAM and PPI dendrimers. Dendrimers are manufactured by a repetitive divergent growth technique, allowing the synthesis of successive, well-defined "generations" of homodisperse structures (FIG. 1). The potency of both PAMAM and PPI dendrimers in eliminating PrP$^{Sc}$ from ScN2a cells increased as the generation level increased. The most potent compounds with respect to eliminating PrP$^{Sc}$ were PAMAM generation 4.0 and PPI generation 4.0, whereas PAMAM generation 1.0 showed very little ability to eliminate PrP$^{Sc}$ (Table 1). Similarly, a high MW fraction of PEI was more potent than low MW PEI.

From the foregoing data, it is clear that for all three branched polyamines tested, increasing molecular size corresponded to an increased potency for eliminating PrP$^{Sc}$. To determine whether this trend was directly attributable to increased surface density of amino groups on the larger molecules, PAMAM-OH generation 4.0 was tested. This is a dendrimer that resembles PAMAM generation 4.0 except that hydroxyls replace amino groups on its surface. Unlike PAMAM generation 4.0, PAMAM-OH generation 4.0 did not cause a reduction of PrP$^{Sc}$ levels even at the highest concentration tested (10 mg/ml), establishing that the amino groups are required for the elimination of PrP$^{Sc}$ by PAMAM (Table 1).

In an effort to assess the contribution of the branched architecture to the clearing ability of polyamines for PrP$^{Sc}$, the linear molecules poly-(L)lysine and linear PEI were also tested. Both of these linear compounds were less potent than a preparation of branched PEI with similar average molecular weight (Table 1), establishing that a branched molecular architecture optimizes the ability of polyamines to eliminate PrP$^{Sc}$, presumably because the branched structures achieve a higher density of surface amino groups.

Kinetics of PrP$^{Sc}$ Elimination by Polyamines.

The preceding results demonstrate the potent ability of branched polyamines to clear PrP$^{Sc}$ from ScN2a cells within a few hours of treatment. The utility of these compounds to act as therapeutics for treatment of prion disease was tested by determining whether they were cytotoxic for ScN2a cells, using as criteria cell growth, morphology, and viability as measured by trypan blue staining. None of the compounds was cytotoxic to ScN2a cells after exposure for one week at concentrations up to 7.5 μg/ml. To determine whether branched polyamines can cure ScN2a cells of scrapie infection without affecting cell viability, the kinetics of prion clearance was examined in the presence of a non-cytotoxic concentration (7.5 μg/ml) of three different branched polyamines. ScN2a cells were exposed to SuperFect, PEI, or PAMAM generation 4.0 for varying periods of time. The kinetics of PrP$^{Sc}$ elimination were assessed by Western blotting. All three compounds caused a substantial reduction in PrP$^{Sc}$ levels after 8–16 h of treatment, and of the three compounds, PEI appeared to remove PrP$^{Sc}$ most quickly, with a t½=4 h.

Curing Neuroblastoma Cells of Scrapie Infection.

The above results show that it is possible to reverse the accumulation of PrP$^{Sc}$ in ScN2a cells under non-cytotoxic conditions. It was also found that extended exposure to even lower levels of the branched polyamines (1.5 μg/ml) was sufficient to eliminate PrP$^{Sc}$. Based on these findings, this protocol was used to determine whether the severe reduction in PrP$^{Sc}$ levels following exposure to branched polyamines would persist after removal of the compounds. Following the exposure of ScN2a cells to a 1.5 μg/ml SuperFect for 1 week, PrP$^{Sc}$ was reduced to <1% of the baseline level, but then increased back to ~5% of the baseline level after 3 additional weeks in culture in the absence of polyamine. In contrast, following exposure to 1.5 μg/ml of either PEI or PAMAM generation 4.0 for 1 week, PrP$^{Sc}$ was completely eliminated and did not return even after 3 weeks in culture without polyamines. A more intensive course of treatment with 1.8 μg/ml SuperFect for 9 d also cured ScN2a cells of scrapie infection fully, manifested by the absence of PrP$^{Sc}$ 1 month after removal of SuperFect.

Evidence for Polyamines Acting Within an Acidic Compartment.

The above results showed the potent activity of branched polyamines in rapidly clearing scrapie prions from cultured ScN2a cells. Based on these results the mechanism by which these compounds act was investigated. All of the compounds which effect removal of PrP$^{Sc}$ from ScN2a cells are known to traffic through endosomes (Boussif, O., et al. A versatile vector for gene and oligonucleotide transfer into cells in culture and in vivo: polyethyleneimine. *Proc. Natl. Acad. Sci. U.S.A.* 92, 7297–7301 (1995); Haensler, J. & Szoka, F. C. J. Polyamidoamine cascade polymers mediate efficient transfection of cells in culture. *Bioconjug. Chem.* 4, 372–379 (1993)). Since $PrP^C$ is converted into $PrP^{Sc}$ in caveolae-like domains (CLDs) or rafts (Gorodinsky, A. & Harris, D. A. Glycolipid-anchored proteins in neuroblastoma cells form detergent-resistant complexes without caveolin. *J. Cell Biol.* 129, 619–627 (1995); Taraboulos, A., et al. Cholesterol depletion and modification of COOH-terminal targeting sequence of the prion protein inhibits formation of the scrapie isoform. *J. Cell Biol.* 129, 121–132 (1995); Vey, M., et al. Subcellular colocalization of the cellular and scrapie prion proteins in caveolae-like membranous domains. *Proc. Natl. Acad. Sci. USA* 93, 14945–14949 (1996); Kaneko, K., et al. COOH-terminal sequence of the cellular prion protein directs subcellular trafficking and controls conversion into the scrapie isoform. *Proc. Natl. Acad. Sci. USA* 94, 2333–2338 (1997)) and is then internalized through the endocytic pathway (Caughey, B., Raymond, G. J., Ernst, D. & Race, R. E. N-terminal truncation of the scrapie-associated form of PrP by lysosomal protease(s): implications regarding the site of conversion of PrP to the protease-resistant state. *J. Virol.* 65, 6597–6603 (1991); Borchelt, D. R., Taraboulos, A. & Prusiner, S. B. Evidence for synthesis of scrapie prion proteins in the endocytic pathway. *J. Biol. Chem.* 267, 16188–16199 (1992)), it was deduced that polyamines act upon $PrP^{Sc}$ in endosomes or lysosomes. This deduction was investigated by determining the effect of pretreatment with the lysosomotropic agents chloroquine and $NH_4Cl$ on the ability of polyamines to eliminate $PrP^{Sc}$. These lysosomotropic agents alkalinize endosomes and have no effect on $PrP^{Sc}$ levels when administered to ScN2a cells (Taraboulos, A., Raeber, A. J., Borchelt, D. R., Serban, D. & Prusiner, S. B. Synthesis and trafficking of prion proteins in cultured cells. *Mol. Biol. Cell* 3, 851–863 (1992)). Experimental results obtained shows that 100 $\mu$M chloroquine, but not 30 $\mu$M $NH_4Cl$, blocked the ability of PEI to eliminate $PrP^{Sc}$. Similar results were obtained with SuperFect and PAMAM, generation 4.0. Although the failure of $NH_4Cl$ to affect $PrP^{Sc}$ levels is not easily explained, the ability of chloroquine to attenuate the ability of branched polyamines to remove $PrP^{Sc}$ is consistent with the notion that these agents act in endosomes or lysosomes.

ORGAN HOMOGENATE ASSAY

The above results with cell cultures prompted investigating the possibility that in an acidic environment branched polyamines, either by indirectly interacting with $PrP^{Sc}$ or with another cellular component, could cause $PrP^{Sc}$ to become susceptible to hydrolases present in the endosome/lysozome. An in vitro degradation assay was developed to evaluate the effect of pH on the ability of polyamines to render $PrP^{Sc}$ sensitive to protease. Crude homogenates of scrapie-infected mouse brain were exposed to a broad range of pH values in the presence or absence of SuperFect and then treated with proteinase K prior to Western blotting. Whereas $PrP^{Sc}$ remained resistant to protease hydrolysis throughout the pH range (3.6–9.6) in the absence of Superfect, addition of the branched polyamine at pH 4.0 or below caused $PrP^{Sc}$ to become almost completely degraded by protease.

Polyamine addition showed a dramatic effect on clearance in vitro which was optimized at pH 4 or less. These results show that polyamines act on $PrP^{Sc}$ in an acidic compartment. To establish that the in vitro degradation assay is a valid approximation of the mechanism by which branched polyamines enhance the clearance of $PrP^{Sc}$ from cultured cells, a structure activity analysis was performed with several of the compounds tested in culture cells. An excellent correlation was found between the clearance of $PrP^{Sc}$ in cultured ScN2a cells (Table 1) and the ability to render $PrP^{Sc}$ susceptible to protease at acidic pH in vitro. Notably, PAMAM-OH generation 4.0 failed to render $PrP^{Sc}$ susceptible to protease, whereas PAMAM generation 4.0 and PPI, generation 4.0 exhibited an even stronger activity than Superfect in vitro, as expected from their observed potency in cultured ScN2a cells (Table 1).

MECHANISM OF ACTION

The results discussed here show that certain branched polyamines cause the rapid elimination of $PrP^{Sc}$ from ScN2a cells in a dose- and time-dependent manner. These compounds demonstrate a potent ability to remove prions from cultured cells at concentrations that are completely non-cytotoxic. The cells may be maintained indefinitely in culture in the presence of therapeutic levels of branched polyamines. Furthermore, when ScN2a cells were exposed to these compounds for ~1 week, $PrP^{Sc}$ was reduced to undetectable levels and remained so for at least one month after removal of the polyamine.

Clarification of the exact mechanism of $PrP^{Sc}$ elimination by branched polyamines is an important objective. Although a number of possible scenarios exist, several possibilities may be excluded already. One possibility that was eliminated was that polyamines act by induction of chaperones such as heat shock proteins that mediate prion protein refolding because the above results show that it was possible to reproduce the phenomenon in vitro. Furthermore polyamines seem to offer advantages over other putative therapeutics that would seek to promote refolding: at very high concentrations, dimethyl sulfoxide (DMSO) and glycerol act as direct "chemical chaperones" and inhibit the formation of new $PrP^{Sc}$ (Tatzelt, J., Prusiner, S. B. & Welch, W. J. Chemical chaperones interfere with the formation of scrapie prion protein. *EMBO J.* 15, 6363–6373 (1996)), but these compounds cannot reduce pre-existing $PrP^{Sc}$ levels. Furthermore, polyamines inhibit $PrP^{Sc}$ formation at much lower concentrations than these agents. The ability of polyamines to effect the rapid clearance of $PrP^{Sc}$ also contrasts with the activity of other potential prion therapeutics. Sulfated polyanions may inhibit $PrP^{Sc}$ accumulation in ScN2a cells by directly binding to $PrP^C$ (Gabizon, R., Meiner, Z., Halimi, M. & Ben-Sasson, S. A. Heparin-like molecules bind differentially to prion-proteins and change their intracellular metabolic fate. *J. Cell. Physiol.* 157, (1993); Caughey, B., Brown, K., Raymond, G. J., Katzenstein, G. E. & Thresher, W. Binding of the protease-sensitive form of PrP (prion protein) to sulfated glycosaminoglycan and Congo red. *J. Virol.* 68, 2135–2141 (1994)), but because branched polyamines are able to clear pre-existing $PrP^{Sc}$, their mechanism of action cannot simply involve binding to $PrP^C$ and inhibiting de novo synthesis.

Another possible mechanism which can be excluded is endosomal rupture. The branched polyamines which were effective in clearing $PrP^{Sc}$ from ScN2a cells in our experiments, PEI, SuperFect and PAMAM, are also potent lysosomotropic, osmotic agents which can swell in acidic environments and rupture endosomes (Boussif, O., et al. A versatile vector for gene and oligonucleotide transfer into cells in culture and in vivo: polyethyleneimine. *Proc. Natl.*

Acad. Sci. U.S.A. 92, 7297–7301 (1995); Haensler, J. & Szoka, F. C. J. Polyamidoamine cascade polymers mediate efficient transfection of cells in culture. *Bioconjug. Chem.* 4, 372–379 (1993)). This might suggest that branched polyamines clear $PrP^{Sc}$ from ScN2a cells by rupturing endosomes and exposing $PrP^{Sc}$ to cytosolic degradation processes. However, it is known that the lysosomotropic, endosome-rupturing agents $NH_4Cl$, chloroquine, and monensin do not interfere with the formation of $PrP^{Sc}$ in ScN2a cells (Taraboulos, A., Raeber, A. J., Borchelt, D. R., Serban, D. & Prusiner, S. B. Synthesis and trafficking of prion proteins in cultured cells. *Mol. Biol. Cell* 3, 851–863 (1992)). Furthermore, the results also show that chloroquine interferes with the ability of branched polyamines to clear $PrP^{Sc}$ and that polyamines can clear $PrP^{Sc}$ in vitro at acidic pH in the absence of cell membranes. Together, these observations rule out endosome rupture as the mechanism by which branched polyamines remove $PrP^{Sc}$.

Without committing to any particular mechanism of action it appears likely that branched polyamines require the acidic environment of intact endosomes or lyzosomes to destroy $PrP^{Sc}$. The structure-activity profile of polymers tested reveals that the most active compounds possess densely packed, regularly-spaced amino groups, suggesting that these compounds may bind to a ligand which has periodically-spaced negative charges. Several scenarios remain possible. (1) Branched polyamines may bind directly to $PrP^{Sc}$ arranged as an amyloid with exposed negatively-charged moieties and induce a conformational change under acidic conditions. (2) Treatment of PrP 27–30 with acid decreases turbidity and increases a-helical content, suggesting that such conditions might dissociate $PrP^{Sc}$ into monomers (Safar, J., Roller, P. P., Gajdusek, D. C. & Gibbs, C. J., Jr. Scrapie amyloid (prion) protein has the conformational characteristics of an aggregated molten globule folding intermediate). It is therefore possible that polyamines bind to an equilibrium unfolding intermediate of $PrP^{Sc}$ present under acidic conditions. (3) Alternatively, polyamines might sequester a cryptic, negatively charged component bound to $PrP^{Sc}$ that is essential for protease resistance, but which is only released when $PrP^{Sc}$ undergoes an acid-induced conformational change. Such a component might act as a chaperone for $PrP^{Sc}$ inside endosomes or lysosomes. (4) Finally, another possibility is that polyamines activate an endosomal or lysosomal factor which can induce a conformational change in $PrP^{Sc}$. Clearly, more work will be required to determine the precise mechanism by which branched polyamines destroy $PrP^{Sc}$.

GENERAL APPLICABILITY OF ASSAY

The in vitro assay described here is generally applicable in the search for drugs that effectively treat as well as prevent a number of degenerative and inherited diseases, where the accumulation of proteins seems to mediate the pathogenesis of these illnesses. By simulating lysosomes, where proteases hydrolyze proteins under acidic conditions, the in vitro brain homogenate assay is able to rapidly evaluate the efficacy of a variety of polyamines to induce degradation of $PrP^{Sc}$.

The in vitro assay which used scrapie infected brain homogenate to test for compounds which clear $PrP^{Sc}$ could be modified to assay for compounds which would clear any conformationally altered protein. The assay is carried out by homogenizing the organ or tissue where the conformationally altered protein is present in the highest concentration. The pH of the homogenate is then reduced to less than 5.0 and preferably 4.0 or less. For example pancreatic tissue can be homogenized to produce an assay to test for compounds which clear amylin which is associated with type II Diabetes. Homogenized kidney could be used to test for compounds which clear $\beta_2$—microglobulin and homogenized heart or vascular tissue used to test for compounds which clear atrial natriuretic factor. Those skilled in the art will recognize other organs and tissue types which can be homogenized to test for other compounds which clear other conformationally altered proteins.

Besides using the in vitro assay to screen for potential drugs, the compounds found via the assay such as branched polyamines provide a new tool for exploring the conversion of a protein to conformationally altered protein, e.g. $PrP^C$ into $PrP^{Sc}$. The mechanism by which branched polyamines render $PrP^{Sc}$ susceptible to proteolysis, remains to be established. Whether the interaction of branched polyamines with $PrP^{Sc}$ is reversible is unknown. In addition, we do not know whether branched polyamines are able to solubilize $PrP^{Sc}$ without irreversibly denaturing the protein. Whatever the mechanism by which branched polyamines interact with $PrP^{Sc}$, it is likely to be different from that found with chaotropes as well as denaturing detergents and solvents (Prusiner, S. B., Groth, D., Serban, A., Stahl, N. & Gabizon, R. Attempts to restore scrapie prion infectivity after exposure to protein denaturants. *Proc. Natl. Acad. Sci. USA* 90, 2793–2797 (1993)).

Using the assays of the invention certain specific branched polyamines have been found which mediate the clearance of $PrP^{Sc}$ from cultured cells under non-cytotoxic conditions. These compounds offer the intriguing possibility of therapeutic reagents for prion diseases. Since the compound found acts by stimulating normal cellular pathways of protein degradation to destroy $PrP^{Sc}$, this class of compounds would also likely be of value in the treatment of other degenerative and hereditary disorders where abnormally folded, wild-type or mutant proteins accumulate. Such an approach may find merit in developing an effective therapeutics for one or more of the common, degenerative illnesses including Alzheimer's disease, Parkinson's disease, amyotrophic lateral sclerosis, frontotemporal dementia, adult onset diabetes mellitus and the amyloidoses (Beyreuther, K. & Masters, C. L. Serpents on the road to dementia and death. Accumulating evidence from several studies points to the normal function of presenilin 1 and suggests how the mutant protein contributes to deposition of amyloid plaques in Alzheimer's disease. *Nature Medicine* 3, 723–725 (1997); Masters, C. L. & Beyreuther, K. Alzheimer's disease. *BMJ* 316, 446–448 (1998); Selkoe, D. J. The cell biology of beta-amyloid precursor protein and presenilin in Alzheimer's disease. *Trends in Cell Biol.* 8, 447–453 (1998); Selkoe, D. J. Translating cell biology into therapeutic advances in Alzheimer's disease. *Nature* 399, A23–31 (1999); Wong, P. C., et al. An adverse property of a familial ALS-linked SOD1 mutation causes motor neuron disease characterized by vacuolar degeneration of mitochondria. *Neuron* 14, 1105–1116 (1995); Spillantini, M. G., Crowther, R. A., Jakes, R., Hasegawa, M. & Goedert, M. a-Synuclein in filamentous inclusions of Lewy bodies from Parkinson's disease and dementia with Lewy bodies. *Proc. Natl. Acad. Sci. USA* 95, 6469–6473 (1998); Hutton, M., et al. Association of missense and 5'-splice-site mutations in tau with the inherited dementia FTDP-17. *Nature* 393, 702–705 (1998); Stone, M. J. Amyloidosis: a final common pathway for protein deposition in tissues. *Blood* 75, 531–545 (1990)). Whether branched polyamines might also prove efficacious in a variety of inherited disorders where the accumulation of abnormal proteins is a hallmark of the illness remains to be established; these genetic maladies include heritable forms of prion disease, Alzheimer's disease, Parkinson's disease, amyotrophic lateral sclerosis, frontotemporal dementia, Pick's disease and amyloidosis, as well as the triplet repeat diseases including Huntington's disease, spinal cerebellar ataxias and myotonic dystrophy (Fu, Y.-H., et al. An unstable triplet repeat in a gene related to myotonic muscular dystrophy. *Science* 255, 1256–1259 (1992); Group, T.H.s-.D.C.R. A novel gene containing a trinucleotide repeat that is expanded and unstable on Huntington's disease chromosomes. *Cell* 72, 971–983 (1993)). Compounds identified via assays of the invention such as branched polyamines will find utility in preventing or delaying the onset of these genetic diseases where carriers can often be identified decades in advance of detectable neurologic or systemic dysfunction.

The invention is based on the discovery that several dendritic polycations, including the starburst dendrimers Superfect™ (QIAGEN®, Valencia, Calif.), polyamidoamide (PAMAM), and the hyperbranched polycation polyethyleneimine (PEI), were surprisingly found to eliminate $PrP^{Sc}$ from cultured scrapie-infected neuroblastoma cells. These highly-branched, polycationic compounds provide a novel class of therapeutic agents to combat prion diseases and other degenerative disease including the amyloidoses. The removal of $PrP^{Sc}$ is dependent on both the concentration of dendritic polymer and length of exposure. Dendritic polymers were able to clear $PrP^{Sc}$ at concentrations which were not cytotoxic. Repeated exposures to heat-degraded starburst PAMAM dendrimer or PET caused a dramatic reduction in $PrP^{Sc}$ levels which persisted for a month even after removal of the compound. Dendritic polycations did not appear to destroy purified $PrP^{Sc}$ in vitro, and therefore may act through a generalized mechanism. Dendritic polycations represent a class of compounds which can be used as therapeutic agents in prion diseases and other disorders involving insoluble protein deposits, such as the amyloidoses.

DENDRIMER COMPOUNDS OF THE INVENTION

Dendrimers are branched compounds also known as "starburst" or "star" polymers due to a characteristic star-like structure (see FIG. 1). Dendrimers of the invention are polymers with structures built from $AB_n$ monomers, with $n \geqq 2$, and preferably n=2 or 3. Such dendrimers are highly branched and have three distinct structural features: 1) a core, 2) multiple peripheral end-groups, and 3) branching units that link the two. Dendrimers may be cationic (full generation dendrimers) or anionic (half generation dendrimers). For a review on the general synthesis, physical properties, and applications of dendrimers, see, e.g., Tomalia et. al, Angew. *Chem. Int. Ed. Engl.*, 29:138–175, (1990); Y. Kim and C.

Zimmerman, *Curr Opin Chem Biol*, 2:733–7421 (1997).

In a preferred embodiment, the pharmaceutical compositions of the invention comprise a cationic dendrimer. Examples of suitable dendrimers are disclosed in U.S. Pat. Nos. 4,507,466, 4,558,120, 4,568,737, 4,587,329, 4,631,337, 4,694,064, 4,713,975, 4,737,550, 4,871,779, and 4,857,599 to D. A. Tomalia, et al., which are hereby incorporated by reference to disclose and describe such compounds. Dendrimers typically have tertiary amines which have a pKa of 5.7. The dendrimers can optionally be chemically or heat treated to remove some of the tertiary amines. Other suitable cations include polypropylene imine, polyethyleneimine (PEI), which has tertiary amines with a pKa of 5.9, and poly(4'-aza-4'-methylheptamethylene D-glucaramide), which has tertiary amines with a pKa of 6.0.

Preferably, the dendrimers for use in the invention are polyamidoamines (hereinafter "PAMAM"). PAMAM dendrimers are particularly biocompatible, since polyamidoamine groups resemble peptide bonds of proteins.

Dendrimers are prepared in tiers called generations (see generations 0, 1 and 2 in FIG. 1) and therefore have specific molecular weights. The full generation PAMAM dendrimers have amine terminal groups, and are cationic, whereas the half generation dendrimers are carboxyl terminated. Full generation PAMAM dendrimers are thus preferred for use in the present invention. PAMAM dendrimers may be prepared having different molecular weights and have specific values as described in Table 1 below for generations 0 through 10.

TABLE A

LIST OF PAMAM DENDRIMERS AND THEIR MOLECULAR WEIGHTS (Ethylene Diamine core, amine terminated).

| GENERATION | TERMINAL GROUPS | MOL. WT. g/mole |
|---|---|---|
| 0 | 4 | 517 |
| 1 | 8 | 1430 |
| 2 | 216 | 3256 |
| 3 | 32 | 6909 |
| 4 | 64 | 14,215 |
| 5 | 128 | 28,795 |
| 6 | 256 | 58,048 |
| 7 | 512 | 116,493 |
| 8 | 1024 | 233,383 |
| 9 | 2048 | 467,162 |
| 10 | 4096 | 934,720 |

As shown in Table A, the number of terminal amine groups for PAMAM dendrimers generations 0 through 10 range from 4 to 4,096, with molecular weights of from 517 to 934,720. PAMAM dendrimers are available commercially from Aldrich or Dendritech. Polyethyleneimine or polypropylene dendrimers or quatemized forms of amine-terminated dendrimers may be prepared as described by Tomalia et. al, Angew, *Chem. Int. Ed. Engl.*, 29:138–175 (1990).

PHARMACEUTICAL COMPOSITION

As demonstrated in the Examples below, highly-branched polycations, e.g. dendrimer compounds, affect the extent and distribution of $PrP^{Sc}$ protein deposits in scrapie-infected cells. The presence of dendrimers at relatively low, non-cytotoxic levels results in a significant reduction in detectable $PrP^{Sc}$ in cells and brain homogenates. Thus, the present invention encompasses pharmaceutical compositions for reducing, inhibiting, or otherwise mitigating plaque formation in a subject susceptible to neuronal degenerative disorders associated with protein deposit formation. A formulation of the invention is comprised of any compound identified via an assay of the invention, (e.g. a polycationic dendrimer) in a pharmaceutically acceptable carrier.

Formulations

Pharmaceutical formulations of the invention preferably contain highly branched polycations, e.g. polycationic dendrimer, in a concentration from 0.1 to 10% of the formulation. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol. The formulations may also contain conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

For use in the subject methods, the highly-branched polycations, e.g. dendrimers, may be formulated with other pharmaceutically active agents, particularly other agents that can modulate onset or symptoms of the condition to be treated. For example, to treat Alzheimer's disease or CAA, the polycation compound can be co-administered with one or more biologically active agents that reduce protein deposit formation and/or prevent protein deposit formation. Examples of such compounds include nonsteroid antiinflammatory drugs (NSAIDs) or aspirin-like drugs (J. R. Vane, *Semin Arthritis Rheum* 26:2–10 (1997)), selective inhibitors of COX-2 (J. R. Vane *Int J Tissue React*, 20:3–15 (1998)), protein phosphatases that act on microtubule-associated protein tau protein phosphatases (K. Iqbal, *Ann N Y Acad Sci* 777:132–8 (1996)), modulators of APP proteolytic enzymes and apoE activity (P. T. Lansbury Jr, *Arzneimittelforschung* 45:432–4 (1995)), inhibitors of polysaccharides, such as glycosaminoglycan and proteoglycans, (B. Leveugle et al., *Neuroreport* 5:1389–92 (1994)) and the like. The additional active ingredients may be conjugated to the branched polycation or may be contained separately within a formulation.

The formulations of the invention have the advantage that they are non-toxic in tested forms of administration. For example, parenteral administration of a solution of the formulations of the invention is preferably nontoxic at a dosage of 0.1 mg/mouse, which is an $LD_{50}$ of less than one at 40 mg/Kg. Various injectable formulations of the type known to those skilled in the art can be used to delivery compounds of the invention.

Administration

Administration of a compound of the invention may be accomplished by any convenient means, including any type of injection including parenteral injection, and direct intracerebral injection or continuous (e.g., long-term or chronic) infusion. The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intratracheal, etc., administration. The active agent may be systemic after administration or may be localized by the use of regional administration, intramural administration, or use of an implant that acts to retain the active dose at the site of implantation.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing sensitizer is placed in proximity to the site of protein deposits (e.g., the site of formation of amyloid deposits associated with neurodegenerative disorders), so that the local concentration of active agent is increased at that site relative to the rest of the body.

The formulations can also be administered by infusion into the brain, and may be administered in either a continuous (e.g., sustained) or non-continuous fashion. Methods, formulations, and devices suitable for delivery to the brain in a continuous (e.g., chronic) or non-continuous (e.g., single, discrete dose per administration) fashion are described in, for example, U.S. Pat. Nos. 5,711,316; 5,832, 932; 5,814,014; 5,782,798; 5,752,515; 5,735,814; 5,713, 923; 5,686,416; 5,624,898; 5,624,894; 5,124,146; and 4,866,042 (delivery of genetic material).

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosage

Depending on the patient and condition being treated and on the administration route, the compounds of the invention will generally be administered in dosages of 0.001 mg to 5 mg/kg body weight per day. The range is broad, since in general the efficacy of a therapeutic effect for different mammals varies widely with doses typically being 20, 30 or even 40 times smaller (per unit body weight) in man than in animal models (e.g., in the transgenic mice described herein). Similarly the mode of administration can have a large effect on dosage. Thus for example oral dosages in the mouse may be ten times the injection dose. Still higher doses may be used for localized routes of delivery.

A typical dosage may be: a solution suitable for intravenous administration; a tablet taken from two to six times daily; or a one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

Natural Products

There are currently available a number of products which are derived from natural sources. Examples include pharmaceuticals derived from blood products. These products are tested for virus and bacteria but are not tested for the presence of conformationally altered proteins. Accordingly, one aspect of the invention is any naturally derived product in combination with a compound of the invention which clears a conformationally altered protein, e.g. blood plasma combined with a polycation, preferably a branched polycation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

METHODS AND MATERIALS

Chemicals. High molecular weight PEI was purchased from Fluka. DOTAP cationic lipid was purchased from Boehringer Mannheim and SuperFect transfection reagent was purchased from QIAGEN®. All other compounds were purchased from Sigma-Aldrich. All test compounds were dissolved in water at stock concentration of 3 mg/ml and filtered through a Millipore 0.22 m m filter.
Cultured Cells.

Stock cultures of ScN2a cells were maintained in MEM with 10% FBS, 10% Glutamax (Gibco BRL), 100 U penicillin, and 100 mg/ml streptomycin (supplemented DME). Immediately prior to addition of test compounds, the dishes were washed twice with fresh supplemented DME media. After exposure to test compounds, dishes were drained of media and cells were harvested by lysis in 0.25–1 ml 20 mM Tris pH 8.0 containing 100 mM NaCl, 0.5% NP-40, and 0.5% sodium deoxycholate to obtain a total protein concentration of 1 mg/ml measured by the BCA assay. Nuclei were removed from the lysate by centrifugation at 2000 rpm for 5 min. For samples not treated with proteinase K, 40 $\mu$l of whole lysate (representing 40 $\mu$g total protein) was mixed with an equal volume of 2×SDS reducing sample buffer. For proteinase K digestion, 20 $\mu$g/ml proteinase K (Boehringer Mannheim) (total protein:enzyme ratio=50:1) was added, and the sample was incubated for 1 h at 37° C. Proteolytic digestion was terminated by the addition of Pefabloc to a final concentration of 5 mM. One ml samples were centrifuged at 100,000×g for 1 h at 4° C., the supernatants were discarded, and the pellets were resuspended in 80 $\mu$l of reducing SDS sample buffer for SDS-PAGE.
Brain Homogenates.

Brain homogenates from RML scrapie-affected CD-1 mice (10% (w/v) in sterile water) were prepared by repeated extrusion through syringe needles of successively smaller size, from 18 to 22 gauge. Nuclei and debris were removed by centrifugation at 1000×g for 5 min. The bicinchnoninic acid (BCA) protein assay (Pierce) was used to determine protein concentration. Homogenates were adjusted to 1 mg/ml protein in 1% NP-40. For reactions, 0.5 ml homogenate was incubated with 25 ml 1.0 M buffer (sodium acetate for pH 3–6 and Tris acetate for pH 7–10) plus or minus 10 ml of polyamine stock solution (3 mg/ml) for 2 h at 37° C. with constant shaking. The final pH value of each sample was measured directly with a calibrated pH electrode (Radiometer Copenhagen). Following incubation, each sample was neutralized with an equal volume 0.2 M HEPES pH 7.5 containing 0.3 M NaCl and 4% Sarkosyl. Proteinase K was added to achieve a final concentration of 20 $\mu$g/ml, and samples were incubated for 1 h at 37° C. Proteolytic digestion was terminated by the addition of Pefabloc to a final concentration of 5 $\mu$M. Ten $\mu$l of digested brain homogenate was mixed with equal volume 2×SDS sample buffer and analyzed by SDS-PAGE followed by Western blotting.
Western Blotting.

Following electrophoresis, Western blotting was performed as previously described (Scott, M., et al. Transgenic mice expressing hamster prion protein produce species-specific scrapie infectivity and amyloid plaques. *Cell* 59, 847–857 (1989)). Samples were boiled for 5 min and cleared by centrifugation for 1 min at 14,000 rpm in aBeckman ultrafuge. SDS-PAGE was carried out in 1.5 mm, 12% polyacrylamide gels(Laemmli, U. K. Cleavage of structural proteins during the assembly of the head of bacteriophage T-4. *Nature* 227, 680–685 (1970)). Membranes were blocked with 5% non-fat milk protein in PBST (calcium— and magnesium—free PBS plus 0.1% Tween 20) for 1 h at room temperature. Blocked membranes were incubated with primary RO73 polyclonal antibody (to detect MoPrP) (Serban, D., Taraboulos, A., DeArmond, S. J. & Prusiner, S. B. Rapid detection of Creutzfeldt-Jakob disease and scrapie prion proteins. *Neurology* 40, 110–117 (1990)) or 3F4 monoclonal antibody (to detect MHM2 PrP) (Kascsak, R. J., et al. Mouse polyclonal and monoclonal antibody to scrapie-associated fibril proteins. *J. Virol.* 61, 3688–3693 (1987)) at 1:5000 dilution in PBST overnight at 4° C. Following incubation with primary antibody, membranes were washed 3×10 min in PBST, incubated with horseradish peroxidase-labeled secondary antibody (Amersham Life Sciences) diluted 1:5000 in PBST for 30 to 60 min at 4° C. and washed again for 3×10 min in PBST. After chemiluminescent development with ECL reagent (Amersham) for 1 min, blots were sealed in plastic covers and exposed to ECL Hypermax film (Amersham). Films were processed automatically in a Konica film processor.

EXAMPLE 1A

Branched Polyamines Inhibit Formation of Nascent PrP$^{Sc}$ and Induce Clearance of Pre-existing PrP$^{Sc}$ Western blots were probed with 3F4 monoclonal antibody which recognizes newly expressed MHM2 PrP. ScN2a cells were exposed to SuperFect for 3 h and harvested 3 d after removal of SuperFect. Gels were run on both undigested, control sample and a sample subjected to limited proteolysis. The samples were run in separate lanes 1–6 with a control and limited proteolysis sample for each of the 6 lanes as follows: Lane 1: DOTAP-mediated transfection. Lane 2: 30 μg/ml SuperFect, 5 μg pSPOX MHM2. Lane 3: 75 μg/ml SuperFect, 5 μg pSPOX MHM2. Lane 4: 150 μg/ml SuperFect, 5 μg pSOX MHM2. Lane 5: 150 μg/ml SuperFect, 10 μg pSPOX MHM2. Lane 6: No addition of either transfection reagent or DNA. Forty μl of undigested brain homogenate was used in these studies while those samples subjected to limited digestion with proteinase K were concentrated 25-fold prior to SDS-PAGE. One ml of the digest were centrifuged at 100,000×g for 1 h at 4° C. and the pellets suspended in 80 μl of SDS sample buffer prior to SDS-PAGE followed by Western blotting. Apparent molecular weights based on migration of protein standards are 34.2, 28.3, and 19.9 kDa.

All of the control lanes 1–6 show multiple bands as expected. However, of the samples subjected to limited proteolytic only lane 1 shows bands. Unexpectedly, all of the partially digested sample lanes 2–5 show no bands and as expected no bands in the partially digested lane 6. These results show the effect of using SuperFect in clearing PrP$^{Sc}$.

EXAMPLE 1B

The blot described above was stripped of antibody, exposed to labeled RO73 and redeveloped. The antibody 3F4 used in Example 1 binds to PrP$^C$ but not to PrP$^{Sc}$. However, RO73 binds to PrP$^{Sc}$ and PrP$^C$. Lanes 1, 2 and 3 show decreasing amounts of PrP$^{Sc}$ and lanes 4 and 5 show no detectable PrP$^{Sc}$.

EXAMPLE 2A

Gels were run on undigested controls 1–4 and as above, samples subjected to limited proteolysis. The lanes were as follows: Lane 1: No SuperFect. Lane 2: 30 μg/ml SuperFect. Lane 3: 75 μg/ml SuperFect. Lane 4: 150 μg/ml SuperFect. ScN2a cells were exposed to SuperFect for 3 h and harvested 3 d after removal of SuperFect. Apparent molecular weights based on migration of protein standards are 33.9, 28.8, and 20.5 kDa. In that each sample was tested after the same time period the results show the dose-dependent effect of SuperFect on PrP$^{Sc}$ removal. Lanes 1, 2 and 3 show decreasing amounts of PrP$^{Sc}$ and lane 4 shows no detectable PrP$^{Sc}$.

EXAMPLE 2B

To determine the time-dependent effect of SuperFect three different panels with four lanes each were prepared and run as follows: ScN2a cells were exposed to 7.5 μg/ml: SuperFect (lanes 1–4), PEI (average molecular weight ~60,000) (lanes 5–8), or PAMAM, generation 4.0 (lanes 9–12). Time of exposure times for each polyamine: 0 hours (lanes 1, 5, and 9), 4 hours (lanes 2, 6, and 10), 8 hours (lanes 3, 7, and 11), 16 hours (lanes 4, 8, and 12). All samples were subjected to limited proteolysis to measure PrP$^{Sc}$. Apparent molecular weights based on migration of protein standards are 38, 26, and 15 kDa. Lanes of each of the three panels show decreasing amounts of PrP$^{Sc}$.

EXAMPLE 3

In this example four panels A,B, C and D were created with panels having three double (control and test) lanes each. ScN2a cells were exposed to 1.5 μg/ml: (A) SuperFect, (B) PEI (average molecular weight ~60,000), (C) PAMAM, generation 4.0, or (D) no addition. Cells were harvested: Lane 1, before addition; Lane 2, immediately following 1 week continuous exposure to test compounds; and Lane 3, three weeks after removal of test compounds. Minus (−) symbol denotes undigested, control sample and plus (+) symbol designates sample subjected to limited proteolysis. Apparent molecular weights based on migration of protein standards are 33.9, 28.8, and 20.5 kDa. Test lanes 3 in panel A showed slight PrP$^{Sc}$ after three weeks and test lanes 3 in panels B and C showed no detectable PrP$^{Sc}$ whereas PrP$^{Sc}$ was present in all lanes in panel D.

EXAMPLE 4A

Four separate gels were run to demonstrate the effect of adding chloroquine would have on PrP$^{Sc}$ levels. The lanes 1 control and 3 where chloroquine was added show clear bands for PrP$^{Sc}$ whereas lanes 2 and 4 with no chloroquine show barely detectable amounts of PrP$^{Sc}$. The four lanes were prepared as follows: ScN2a cells were treated Lane 1: Control media. Lane 2: 7.5 μg/ml PEI (average molecular weight ~60,000). Lane 3: PEI plus 100 μM chloroquine. Lane 4: PEI plus 30 μM NH$_4$Cl. Chloroquine and NH$_4$Cl were added 1 h prior to addition of PEI. Cells were harvested 16 hours after addition of PEI. All samples shown were subjected to limited proteolysis to measure PrP$^{Sc}$. Apparent molecular weights based on migration of protein standards are 38, 26, and 15 kDa.

EXAMPLE 4B

Eight lanes with SuperFect (+SF) and eight lanes without SuperFect (−SF) were prepared. Lanes 1–8 of each group had an adjusted pH of 3.6, 4, 5, 6, 7, 8, 9 and 9.6. In vitro mixture of crude mouse brain homogenates with SuperFect under a range of pH conditions was performed as described in methods (measured final pH of each sample denoted above the lanes). Addition of 60 μg/ml SuperFect denoted as "+SF" and control with no addition as "−SF". All samples shown were subjected to limited proteolysis to measure PrP$^{Sc}$. Apparent molecular weights based on migration of protein standards are 30 and 27 kDa. All lanes of the −SF group showed PrP$^{Sc}$ present. Lanes 3–8 of the +SF group showed PrP$^{Sc}$. However, lanes 1 and 2 with respective pH levels of 3.6 and 4.0 showed very slight detectable PrP$^{Sc}$. The results show that the ability of a blanched polycation such as SuperFect to clear PrP$^{Sc}$ is pH dependent.

EXAMPLE 5

Sixteen different lanes were prepared as described. Lanes 1 and 2 were control lanes and each of lanes 3–16 contained a different compound as tested in Table 1. The test compounds were all polyamines. Thus, the results show removal of $PrP^{Sc}$ from brain homogenate in vitro by various polyamines. Samples were incubated with polyamines at pH 3.6 and processed as described in Methods. Each polyamine was tested at 60 μg/ml concentration. Lanes 1 and 2: control. Lane 3: poly-(L)lysine. Lane 4: PAMAM, generation 0.0. Lane 5: PAMAM, generation 1.0. Lane 6: PAMAM, generation 2.0. Lane 7: PAMAM, generation 3.0. Lane 8: PAMAM, generation 4.0. Lane 9: PAMAM-OH, generation 4.0. Lane 10: PPI, generation 2.0. Lane 11: PPI, generation 4.0. Lane 12: linear PEI. Lane 13: high MW PEI. Lane 14: low MW PEI. Lane 15: average MW PEI. Lane 16: SuperFect. All samples shown were subjected to limited proteolysis to measure $PrP^{Sc}$. Apparent molecular weights based on migration of protein standards are 30 and 27 kDa.Table 1. Removal of $PrP^{Sc}$ by polymer compounds. $IC_{50}$= approximate concentration of polymer required to reduce $PrP^{Sc}$ to 50% of control levels in ScN2a cells after exposure for 16 hours. All compounds were tested at 5 different concentrations. $PrP^{Sc}$ levels were measured by densitometry of Western blot signals.

TABLE 1

(Note that Table 1 includes information on the characteristics of compounds used but that the list does not correspond directly to lanes 1–16)

| Compound | Molecular Weight | Primary $NH_2$ groups | $IC_{50}$ (ng/ml) |
|---|---|---|---|
| PAMAM generation 0.0 | 517 | 4 | >10,000 |
| PAMAM generation 1.0 | 1,430 | 8 | >10,000 |
| PAMAM generation 2.0 | 3,256 | 16 | 2,000 |
| PAMAM generation 3.0 | 6,909 | 32 | 400 |
| PAMAM generation 4.0 | 14,215 | 64 | 80 |
| PAMAM-OH generation 4.0 | 14,279 | 0 | >10,000 |
| PPI generation 2.0 | 773 | 8 | 2,000 |
| PPI generation 4.0 | 3,514 | 32 | 80 |
| Low MW PEI | ~25,000 | | 2,000 |
| Average MW PEI | ~60,000 | | 400 |
| High MW PEI | ~800,000 | | 80 |
| Linear PEI | ~60,000 | | 2,000 |
| poly-(L)lysine | ~60,000 | >500 | 10,000 |
| SuperFect | | | 400 |

Lanes 7, 8, 11 and 13 showed the best results, i.e. best ability to clear $PrP^{Sc}$ under these conditions. Specifically, PAMAM generation 4.0 in lane 8 showed the best ability to clear $PrP^{Sc}$ under these conditions whereas PAMAM-OH generation 4.0 showed almost no detectable ability to clear $PrP^{Sc}$ and was comparable to the control.

EXAMPLE 6

Transfection of $PrP^{Sc}$ Expressing Cells with Dendrimer Compounds

Cells of neuronal origin expressing $PrP^{Sc}$ were examined for the ability of compounds to suppress $PrP^{Sc}$ formation.

Transfection Studies

Stock cultures of N2a and ScN2a cells were maintained in MEM with 10% FBS, 10% Glutamax (Gibco BRL), 100 U penicillin, and 100 μg/ml streptomycin. Cells from a single confluent 100 mm dish were trypsinized and split into 10 separate 60 mm dishes containing DME plus 10% FBS, 10% Glutamax, 100 U penicillin, and 100 μg/ml streptomycin (supplemented DME) one day prior to transfection. Immediately prior to transfection, the dishes were washed twice with 4 ml supplemented DME media and then drained.

For DOTAP-mediated transfection, 15 μg pSPOX MHM2 was resuspended in 150 μl sterile Hepes Buffered Saline (HBS) on the day of transfection. The DNA solution was then mixed with an equal volume of 333 μg/ml DOTAP (Boehringer Mannheim) in HBS in Falcon 2059 tubes and incubated at room temperature for 10 minutes to allow formation of DNA/lipid complexes. Supplemented DME (2.5 ml) was added to the mixture, and this was then pipetted onto drained cell monolayers. The following day, the medium containing DNA/lipid was removed and replaced with fresh supplemented DME. Cells were harvested three days later.

For Superfect™-mediated transfections/exposures, Superfect™ with or without DNA was added to 1 ml supplemented DME in a Falcon 2059 tube to achieve the specific concentrations needed for each experiment. This mixture was pipetted up and down twice and then onto drained cell monolayers. After exposure for the indicated times, the medium containing Superfect™ was removed and replaced with fresh supplemented DME. Cells were harvested at specified times after removal of Superfect™.

Exposures to PPI (DAB-Am-8, Polypropylenimine octaamine Dendrimer, Generation 2.0 Aldrich 46,072-9), Intact PAMAM (Starburst (PAMAM)Dendrimer, Generation 4. Aldrich 41,244-9), PEI (Sigma), poly-(L)lysine (Sigma), and poly-(D) lysine (Sigma) were performed as described above for Superfect™.

Isolation of Protein from Treated Cells

Cells were harvested by lysis in 1.2 ml of 20 mM Tris pH 8.0 containing 100 mM NaCl, 0.5% NP-40, and 0.5% sodium deoxycholate. Nuclei were removed from the lysate by centrifugation at 2000 rpm for 5 min. This lysate typically had a protein concentration of 0.5 mg/ml measured by the BCA assay. For samples not treated with proteinase K, 40 μl of whole lysate (representing 20 μg total protein) was mixed with 40 μl of 2×SDS sample buffer. For proteinase K digestion, 1 ml of lysate was incubated with 20 μg/ml proteinase K (total protein:enzyme ratio=25:1) for 1 hr at 37° C. Proteolytic digestion was terminated by the addition of 8 μl of 0.5M PMSF in absolute ethanol. Samples were then centrifuged for 75 min in a Beckman TLA-45 rotor at 100,000×g at 4° C. The pellet was resuspended by repeated pipetting in 80 μl of 1×SDS sample buffer. The entire sample (representing 0.5 mg total protein before digestion) was loaded for SDS-PAGE.

Western Blot Analysis

Immunoreactive PrP bands from the DOTAP-mediated transfection were detected before and after digestion with proteinase K with monoclonal antibody 3F4. The construct used to express $PrP^{Sc}$ in the ScN2a cells is MHM2 a chimeric construct that differs from wild-type (wt) MoPrP at positions 108 and 111 (Scott et al., (1992) *Protein Sci.* 1:986–997). Substitution at these positions with the corresponding residues (109 and 112 respectively) from the Syrian hamster (SHa) PrP sequence creates an epitope for 3F4 (Kascsak et al., (1987) *J. Virol.* 61:3688–3693), which does not recognize endogenous wt MoPrP in ScN2a cells and hence facilitates specific detection of the transgene by Western blot.

Following electrophoresis, Western blotting was performed as previously described (Scott et al., (1989) *Cell* 59:847–857). Samples were boiled for 5 minutes and cleared by centrifugation for 1 minute at 14,000 rpm in a Beckman ultrafage. SDS-PAGE was carried out in 1.5 mm, 12% polyacrylamide gels (Laemmli (1970) *Nature* 227:661–665). Membranes were blocked with 5% nonfat milk protein in PBST (calcium- and magnesium-free PBS plus 0.1% Tween 20) for 1 hour at room temperature. Blocked membranes were incubated with primary RO73 polyclonal or 3F4 monoclonal antibody at a 1:5000 dilution in PBST overnight at 4° C.

Following incubation with primary antibody, membranes were washed 3×10 minutes in PBST, incubated with horseradish peroxidase-labeled secondary antibody (Amersham Life Sciences) diluted 1:5000 in PBST for 25 minutes at room temperature and washed again for 3×10 minutes in PBST. After chemiluminescent development with ECL reagent (Amersham) for 1 minute, blots were sealed in plastic covers and exposed to ECL Hypermax film (Amersham). Films were processed automatically in a Konica film processor.

In contrast to DOTAP-transfected cells, ScN2a cells transfected with varying concentrations of Superfect™ and DNA did not appear to contain protease-resistant MHM2. Close scrutiny revealed that, prior to protease digestion, Superfect™-transfected samples express MHM2 bands which are not seen in the background pattern of the control sample. These observations indicate that MHM2 PrP was successfully expressed using Superfect™ transfection reagent, but conversion of MHM2 $PrP^C$ to protease-resistant MHM2 $PrP^{Sc}$ was inhibited by Superfect™.

To examine whether Superfect™ had affected levels of preexisting $PrP^{Sc}$ in ScN2a cells, the Western blot probed with 3F4 antibody was reprobed with polyclonal antibody RO73, which is able to recognize endogenous MoPrP. Remarkably, Superfect™ caused the disappearance of preexisting $MoPrP^{Sc}$ from ScN2a cells in a dose-dependent manner. After treatment with Superfect™, $PrP^{Sc}$ could not be detected in the nuclear fraction, pellet, supernatant, or media. The concentration of Superfect™ required to fully remove preexisting $PrP^{Sc}$ with a three hour exposure was 300 µg/ml, whereas 30 µg/ml was sufficient to interfere with the formation of new MHM2 $PrP^{Sc}$ within the same time frame.

Length of exposure dramatically influenced the ability of Superfect™ to remove $PrP^{Sc}$ from ScN2a cells. Whereas a 3 hour exposure to 150 µg/ml Superfect™ significantly lowered $PrP^{Sc}$ levels in ScN2a cells, exposure for 10 min to the same dose of Superfect™ did not affect $PrP^{Sc}$ levels. When ScN2a cells were exposed to 2 µg/ml Superfect™ continuously for 1 week, $PrP^{Sc}$ disappeared completely.

The conditions tested did not appear to be toxic for the cells. Neither 150 µg/ml Superfect™ for 3 hrs nor 2 µg/ml Superfect™ continuously for 1 week caused any obvious changes in cell morphology, viability, or growth as judged by phase contrast microscopy.

EXAMPLE 7

Elimination of $PrP^{Sc}$ by Repeated Exposures to Superfect™

The duration in the reduction in $PrP^{Sc}$ levels after exposure to Superfect™ was examined, and it was shown that this reduction could persist for extended periods after removal of Superfect™. Following the exposure of ScN2a cells to a single dose of 150 µg/ml Superfect™ for 3 hrs, $PrP^{Sc}$ levels remained low for one week, but returned to near baseline levels after 3 weeks in culture without Superfect™.

In contrast, when ScN2a cells were exposed to 4 separate doses of Superfect™ over the course of 16 days, very little $PrP^{Sc}$ could be detected 4 weeks after the final exposure to Superfect™. This result offers hope that prolonged exposure to Superfect™ may lead to long term cure of scrapie infection in cultured cells.

EXAMPLE 8

Superfect™ does not Destroy $PrP^{Sc}$ Directly

The dendrimer Superfect™ was used to determine if it could exert a similar inhibitory effect on $PrP^{Sc}$ in either crude brain homogenates or purified PrP 27–30 rods. Brain homogenates from normal and scrapie-affected Syrian hamsters (10% (w/v) in sterile PBS) were prepared by repeated extrusion through syringe needles of successively smaller size, from 18 to 22 gauge. Nuclei and debris were removed by centrifugation at 1000×g for 10 min. The bicinchnoninic acid (BCA) protein assay (Pierce) was used to determine protein concentration. Homogenates were adjusted to 10 mg/ml protein with PBS and 50 µl was added to 450 µl of lysis buffer containing 100 mM NaCl, 1 mM EDTA, 0.55% sodium deoxycholate, 0.55% Triton X-100, and 50 mM Tris-HCl pH 7.5. This mixture was then incubated with 0–300 µg/ml Superfect™ for 3 hrs at 37° C. and then centrifuged for 10 min at 14,000 rpm in a Beckman Ultrafuge. The pellet was resuspended in 450 µl lysis buffer without Superfect™. Proteinase K (Boehringer Mannheim) was added to achieve a final concentration of 20 µg/ml, and thus the ratio of total protein/enzyme was 50:1. Samples were incubated for 1 h at 37° C. Proteolytic digestion was terminated by the addition of 8 µl of 0.5 M PMSF in ethanol. Samples were then centrifuged for 75 min in a Beckman TLA-45 rotor at 100,000×g at 4° C. Undigested samples (10 µl) were mixed with an equal volume of 2×SDS sample buffer. For digested samples, the pellet was resuspended by repeated pipetting in 100 µl 1×SDS sample buffer. Twenty µl (equivalent to 100 µg of total protein prior to proteinase K digestion) of each sample was loaded for SDS-PAGE.

PrP 27–30 rods were purified from scrapie-affected Syrian hamster brains and previously described (Prusiner et al., (1983) Cell 35:349–358). Purified rods (3.5 µg/ml) were incubated with or without 900 µg/ml Superfect™ in 100 µl supplemented DME. After 16 hrs at 37° C., the suspension was centrifuged at 100,000×g at 4° C. The pellet was resuspended in 500 µl of buffer containing 1 mg/ml BSA, 100 mM NaCl, 1 mM EDTA, 0.55% sodium deoxycholate, 0.55% Triton X-100, and 50 mM Tris-HCl pH 7.5. Proteinase K was added to achieve a final concentration of 20 µg/ml. Samples were incubated for 1 h at 37° C. Proteolytic digestion was terminated by the addition of 8 µl of 0.5 M Pefabloc (Boehringer Mannheim). Samples were then centrifuged for 75 min at 100,000×g at 4° C. Undigested samples (50 µl) were mixed with an equal volume of 2×SDS sample buffer. For digested samples, the pellet was resuspended by repeated pipetting in 100 µl 1×SDS sample buffer. Forty µl of each sample was loaded for SDS-PAGE.

When Superfect™ was mixed with either crude homogenates of scrapie-affected Syrian hamsters or with purified Syrian hamster PrP 27–30, there was no significant change in the level of proteinase K-resistant $PrP^{Sc}$. These results suggest that the removal of $PrP^{Sc}$ from ScN2a cells by Superfect™ depends on the presence of intact cellular machinery.

EXAMPLE 9

Clearance of $PrP^{Sc}$ Levels by other Dendritic Polycations

The Superfect™ compound is a high molecular weight component of heat-degraded PAMAM Starburst dendrimers, which is a cationic, highly-branched, monodisperse polymers (Tang et al., (1996) *Bioconjugate Chem.* 7:703–714). To identify other potentially useful anti-prion therapeutic agents, we screened three other dendritic polycations and two linear cationic polymers for their ability to clear $PrP^{Sc}$ from ScN2a cells. Among the dendritic macromolecules tested, polyetheleneimine (PEI) was the most potent, removing the majority of $PrP^{Sc}$ from ScN2a cells after 3 hrs when used at a concentration of 10 µg/ml. Intact PAMAM displayed a potency comparable to Superfect™, removing approximately half of the detectable $PrP^{Sc}$ when used at a concentration of 50 µg/ml. In contrast, the dendrimer polypropyleneimine (PPI), poly-(L)lysine, and the linear polycation poly-(D)lysine failed to reduce $PrP^{Sc}$ levels at concentrations between 10–50 µg/ml. These results demonstrate that a branched polymeric architecture is required to clear $PrP^{Sc}$. Furthermore, exposure of ScN2a cells to either PEI or intact PAMAM for one week at a concentration of 1.5 µg/ml completely removes $PrP^{Sc}$, effectively curing the cells of scrapie infection.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of enhancing clearance of a conformationally altered protein from cells, comprising the steps of:
   contacting cells with a polycationic dendrimer compound which enhances clearance of $PrP^{Sc}$; and
   allowing the compound to remain in contact with the cells for a time and under conditions sufficient to allow for clearance of the $PrP^{Sc}$ from the cells wherein the compound and conditions are non-cytotoxic to the cells.

2. The method of claim 1, wherein the polycationic dendrimer compound is selected from the group consisting of polypropylene imine, polyethylencimine (PEI) poly(4'-aza-4'-methylheptamethylene D-glucaramide), polyamidoamines and variants or fragments thereof.

3. The method of claim 1, wherein the cells are cells of brain tissue of a human.

4. The method of claim 1, wherein cells are in a subject suffering from a prion disease.

5. The method of claim 1, wherein the compound is contacted with the cells by being administered to a subject in an amount non-toxic to the subject at a dosage of 0.001 mg to 1 mg/kg body weight per day.

6. The method of claim 1, wherein the cells are in a subject suffering from a prion disorder selected from the group consisting of: bovine spongiform encephalopathy, Creutzfeldt-Jacob Disease, fatal familial insomnia, GSS for Gerstmann-Straussler-Scheinker Disease, kuru and scrapie.

7. A method of enhancing clearance from cells, comprising the steps of:
   contacting cells with a polycationic dendrimer compound which enhances clearance of $PrP^{Sc}$;
   allowing the compound to remain in contact with the cells for a time and under conditions sufficient to allow for clearance of $PrP^{Sc}$ from the cells wherein the compound and conditions are non-cytotoxic to the cells are in a subject suffering from a disease selected from the group consisting of: bovine spongiform encephalopathy, Creutzfeldt-Jacob Disease, fatal familial insomnia, GSS for Gerstmann-Straussler-Scheinker Disease, kuru and scrapie.

8. The method of claim 7 wherein the polycationic dendrimer compound is selected from the group consisting of polypropylene imine, polyethyleneimine (PEI) poly(4'-aza-4'-methylheptamethylene D-glucaramide), polyamidoamines and variants or fragments thereof.

* * * * *